United States Patent
Cardiasmenos et al.

(10) Patent No.: US 7,889,113 B2
(45) Date of Patent: Feb. 15, 2011

(54) MMW CONTRABAND SCREENING SYSTEM

(75) Inventors: Apostle G. Cardiasmenos, Carlisle, MA (US); Paul J. DeLia, Croton on the Hudson, NY (US)

(73) Assignee: L-3 Communications Security and Detection Systems Inc., Woburn, MA (US)

( * ) Notice: Subject to any disclaimer, the term of this patent is extended or adjusted under 35 U.S.C. 154(b) by 1475 days.

(21) Appl. No.: 10/962,693

(22) Filed: Oct. 12, 2004

(65) Prior Publication Data

US 2005/0110672 A1 May 26, 2005

Related U.S. Application Data

(60) Provisional application No. 60/510,438, filed on Oct. 10, 2003, provisional application No. 60/579,966, filed on Jun. 15, 2004.

(51) Int. Cl.
- G01S 13/04 (2006.01)
- G01S 13/88 (2006.01)
- G01S 13/89 (2006.01)
- G01S 13/00 (2006.01)

(52) U.S. Cl. ............ 342/22; 342/27; 342/52; 342/53; 342/55; 342/175; 342/176; 342/179; 342/195

(58) Field of Classification Search ............ 342/21, 342/22, 27, 28, 52–55, 59, 175, 176, 179, 342/190–197, 350, 351, 89, 90; 250/330–334, 250/336.1, 252.1, 486.1; 382/100, 115–127, 382/103, 118; 359/212; 340/573.1, 435; 348/118; 600/430
See application file for complete search history.

(56) References Cited

U.S. PATENT DOCUMENTS 3,076,961 A * 2/1963 Bibbero .................. 342/53
3,380,028 A * 4/1968 Gustafson et al. ......... 342/53

(Continued)

FOREIGN PATENT DOCUMENTS

WO   WO99/21148   * 4/1999

OTHER PUBLICATIONS

"Tadar: Millimetre-Wave People Screening System"; no author given; Smiths Detection/Farran Technology Ltd.; Ballincollig, County Cork, Republic of Ireland; Apr. 29, 2005; posted on Internet at smithsdetection.com.*

(Continued)

*Primary Examiner* — Bernarr E Gregory
(74) *Attorney, Agent, or Firm* — Wolf, Greenfield & Sacks, P.C.

(57) ABSTRACT

An inspection system that can detect contraband items concealed on, in or beneath an individual's clothing. The system employs millimeter wave radiation to detect contraband items. The system is described in connection with a check point security system that includes temperature controlled walls to enhance imaging of contraband items. Also, a millimeter wave camera is used in conjunction with a visible light camera that forms images. To address privacy concerns of displaying images of people made with millimeter wave cameras that effectively "see through" clothes, the millimeter wave images are not displayed directly. Rather, computer processing produces indications of suspicious items from the underlying raw millimeter wave images. The indications of suspicious items are overlaid on the image formed by the visible light camera.

37 Claims, 11 Drawing Sheets

U.S. PATENT DOCUMENTS

| | | | | | |
|---|---|---|---|---|---|
| 3,501,762 | A | * | 3/1970 | Klees | 342/53 |
| 4,050,067 | A | * | 9/1977 | Elmore, Jr. | 342/52 |
| 4,071,843 | A | * | 1/1978 | Marien | 342/55 |
| 4,529,883 | A | | 7/1985 | Yamakawa et al. | |
| 4,999,614 | A | | 3/1991 | Ueda et al. | |
| 5,073,782 | A | * | 12/1991 | Huguenin et al. | 342/179 |
| 5,214,438 | A | | 5/1993 | Brusgard et al. | |
| 5,227,800 | A | * | 7/1993 | Huguenin et al. | 342/179 |
| 5,451,793 | A | * | 9/1995 | Boone | 250/486.1 |
| 5,760,397 | A | | 6/1998 | Huguenin et al. | |
| 5,952,957 | A | * | 9/1999 | Szu | 342/53 |
| 6,061,014 | A | * | 5/2000 | Rautanen et al. | 342/52 |
| 6,181,271 | B1 | | 1/2001 | Hosaka et al. | |
| 6,222,481 | B1 | | 4/2001 | Abrahamson et al. | |
| 6,307,475 | B1 | * | 10/2001 | Kelley | 340/573.1 |
| 6,414,712 | B1 | * | 7/2002 | Wanielik et al. | 348/118 |
| 6,480,141 | B1 | * | 11/2002 | Toth et al. | 342/22 |
| 6,587,246 | B1 | * | 7/2003 | Anderton et al. | 359/212 |
| 6,670,912 | B2 | | 12/2003 | Honda | |
| 6,720,905 | B2 | | 4/2004 | Levitan et al. | |
| 6,791,487 | B1 | | 9/2004 | Singh et al. | |
| 6,850,183 | B2 | | 2/2005 | Reeves et al. | |
| 6,870,162 | B1 | * | 3/2005 | Vaidya | 250/330 |
| 6,876,322 | B2 | * | 4/2005 | Keller | 342/22 |
| 6,878,939 | B2 | * | 4/2005 | Vaidya | 250/336.1 |
| 6,888,447 | B2 | * | 5/2005 | Hori et al. | 340/435 |
| 6,894,636 | B2 | * | 5/2005 | Anderton et al. | 342/22 |
| 6,900,438 | B2 | * | 5/2005 | Vaidya et al. | 250/336.1 |
| 6,937,182 | B2 | * | 8/2005 | Lovberg et al. | 342/22 |
| 7,075,080 | B2 | * | 7/2006 | Vaidya | 250/336.1 |
| 7,132,649 | B2 | * | 11/2006 | Vaidya | 250/252.1 |
| 2001/0031068 | A1 | * | 10/2001 | Ohta et al. | 382/103 |
| 2003/0179126 | A1 | | 9/2003 | Jablonski et al. | |
| 2003/0184467 | A1 | | 10/2003 | Collins | |
| 2004/0041724 | A1 | | 3/2004 | Levitan et al. | |
| 2004/0051659 | A1 | | 3/2004 | Garrison | |
| 2004/0056790 | A1 | | 3/2004 | Lovberg et al. | |
| 2004/0263379 | A1 | | 12/2004 | Keller | |
| 2005/0110672 | A1 | | 5/2005 | Cardiasmenos et al. | |

OTHER PUBLICATIONS

A.H. Lettington et al., "Design and development of a high performance passive mm-wave imager for aeronautical applications"; no date given; no publication listed for the paper.*

Clark, et al., "A Real-Time Wide Field of View Passive Millimeter-Wave Imaging Camera," *IEEE Computer Society*, Proceedings of the 32nd Applied Imagery Pattern Recognition Workshop (Apr. 2003).

Korneev, et al., "Passive Millimeter Wave Imaging System With White Noise Illumination for Concealed Weapons Detection," *IEEE*, Imaging and Imaging Applications, 2004, pp. 741-742.

Search Report and Written Opinion of the International Searching Authority received in PCT/US04/33542.

http://www.spie.org/web/abstracts/3000/3064.html,, Spie Proceedings vol. 3064, pp. 1-17.

http://www.millivision.com/products./html, Millivision: "Concealed Threat Detector," pp. 1, Jan. 13, 2005.

http://www.millivision.com, Millivision Inc., Millimeter Wave Technology—Imaging Systems, pp. 1, Jan. 13, 2005.

http://www.qinetiq.com/home/markets/security/transport_security/aviation_security/security, "QinetiQ Airport Passenger Security—ceramics and metal detectors," pp. 1, Jan. 13, 2005.

http://www.farran.com, "Millimimeter Wave Components & Subsystems" pp. 1-2, Jan. 13, 2005.

http://www.tadarvision.com, "Tarar by Farran Technology," pp. 1, Jan. 13, 2005.

http://www.millivision.com, Millivision Inc.: Millimeter Wave Technology—Imaging Systems, pp. 1, Jan. 12, 2005.

H.M. Chen et al, "Automatic Two-Stage IR and MMW Image Registration Algorithm for Concealed Weapons Detection"; IEE Proceedings on vision, Image and Signal Processing; vol. 148, issue 4; pp. 209-216; Aug. 2001; Digital Object Identifier: 10.1049/ip-vis:20010459.

* cited by examiner

MMW CONTRABAND SCREENING SYSTEM

RELATED APPLICATIONS

This application claims priority under 35 U.S.C. §119(e) to U.S. Provisional Application Ser. No. 60/510,438, entitled "DUAL IMAGE PLANE QUASIOPTICAL MMW ENHANCED CAMERA," filed on Oct. 10, 2003, and U.S. Provisional Application Ser. No. 60/579,966, entitled "MMW CONTRABAND SCREENING SYSTEM," filed on Jun. 15, 2004, which are herein incorporated by reference in their entireties.

BACKGROUND OF INVENTION

1. Field of Invention

This invention relates to security systems and more specifically security systems that can detect concealed weapons, explosives or other types of contraband objects that may be carried by a person on, under, or within his clothing.

2. Discussion of Related Art

Because of the threat of terrorism, it is desirable to have a way to detect explosives, weapons or other contrabands concealed by individuals on their persons. The approaches traditionally used to inspect luggage or other containers for contraband are generally not suitable for detecting contraband concealed by individuals on their persons. Most known inspection techniques employ ionizing radiation to form images of items under inspection. Human operators or computer systems programmed with image analysis algorithms can study these images to detect contraband objects concealed within containers.

Because of health risks imposed by ionizing radiation, similar systems may not be used to detect contraband items concealed by people, for example, beneath their clothing. Even imaging systems that employ non-ionizing radiation are not desirable. Many people object to being irradiated, even if the level or frequency of the radiation is not associated with any known health risk.

It has been proposed to use millimeter waves ("mm waves") to image people for contraband detection. However, mm wave cameras can produce images of people in which their clothes are not visible. Such a system may also be objectionable to the people who would be inspected by it.

It would be desirable to have an improved contraband detection system.

SUMMARY OF INVENTION

In one aspect, the invention relates to a contraband detection system having a first camera having a first field of view, the first camera having an output providing first image data representative of radiation in a first frequency band from items in the first field of view. The system includes a second camera having a second field of view at least partially overlapping the first field of view, the second camera having an output providing second image data representative of radiation in a second frequency band, different from the first frequency band, representative of items in the second field of view. A display station coupled to the first camera and the second camera receives the first image data and the second image data and is programmed with at least one computer programmed to present a display of items in the first field of view using the first image data selectively overlaid with an indication of at least one item derived from the second image data.

In another aspect, the invention relates to a method of operating a contraband detection system that includes imaging a person with a millimeter wave camera to produce millimeter wave image data and imaging a person with a second camera to produce visible image data; processing at least the millimeter wave image data to identify a contraband item; and when a contraband item is identified, displaying a visible image of the person using the visible image data overlaid with an indication of the contraband item.

In yet another aspect, the invention relates to a contraband detection system with a heated structure and a millimeter wave camera facing the heated structure.

In a further aspect, the invention relates to a method of operating a contraband detection system that includes providing a millimeter wave camera with a field of view; illuminating the field of view with a millimeter wave signal having a plurality of spatially independent and quasi-random phase and amplitude components; collecting image data with the millimeter wave camera; and using the image data to determine whether contraband items are in the field of view.

In a further aspect, the invention relates to an airport security checkpoint that has an enclosure having a millimeter wave camera imaging a field of view within the enclosure, the enclosure having a passage sized to allow a person to enter the field of view, the camera having a camera data output. The checkpoint also has a baggage scanner having a scanner data output; and at least one computer having inputs coupled to the camera data output and the scanner data output, the at least one computer programmed to present, based on the camera data output and the scanner data output, a threat assessment for a passenger.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
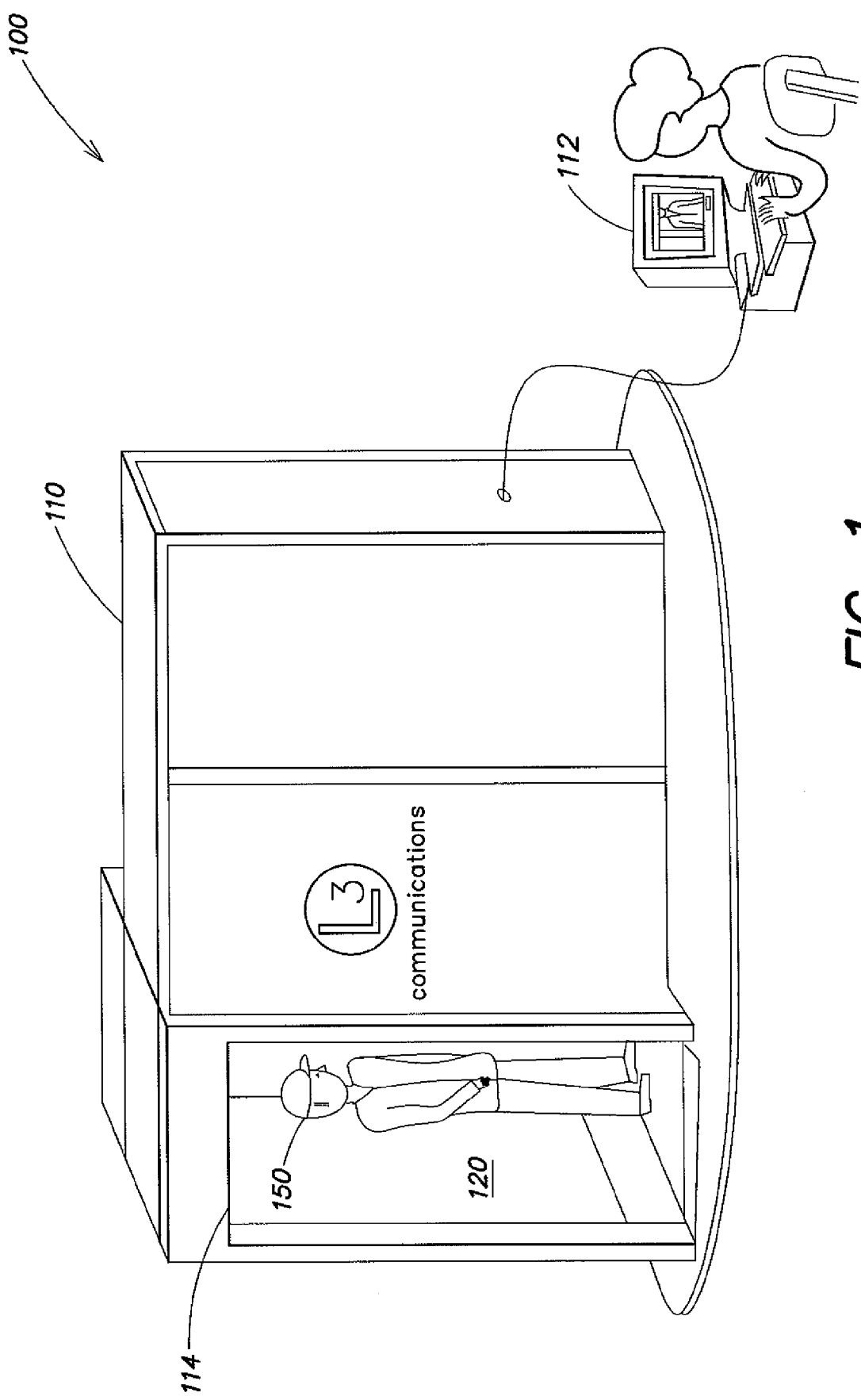
FIG. 1 is a sketch of a millimeter wave inspection system.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

FIG. 1 illustrates an inspection system 100 such as may be used at an airport to screen passengers boarding airplanes. The invention is generally applicable in any situation in which it is desirable to locate contraband items, such as may be carried on, in or under the clothing of an individual being scanned. The invention will be explained using a security checkpoint at an airport as an example application.

Inspection system 100 includes a portal 110 and an operator inspection station 112. Portal 110 includes a doorway 114 through which a person 150 being screened enters the portal 110. Preferably, a similar sized opening is provided on the opposite side of portal 110 to allow the person to exit portal 110. However, it is possible that a portal could be constructed with a single opening, requiring the person to enter and exit the portal through the same opening. Two openings provide more convenient movement of individuals through portal 110. For example, individuals may line up for screening on one side of portal 110. People may pass continuously through the portal, with those cleared by the screening being allowed to pass the security checkpoint. Those not cleared by the screening may be diverted upon exiting portal 110 for further inspection or other steps to ensure they are not carrying contraband. Two openings also facilitates environmental control within portal 110, such that the inside of the portal is at the same temperature and/or relative humidity as the surrounding environment.

In use, a person 150 steps into the portal and stands in front of back wall 120. A visible image is formed of the person against back wall 120 and processed for display on operator station 112. At the same time, the system scans the region near to and over the surface of the person and measures the strength of the millimeter wave radiation emanating from the person and the nearby regions. Preferably, this radiation is presented in the form of a millimeter wave image. The measured values of the millimeter wave radiation are sent to operator station 112 where an embedded automatic target recognition algorithm may process the measured values to determine if contraband items are present on, in or under the clothing covering the individual being scanned.

Preferably, once the visible and passive millimeter wave images of the front of a person are formed, the person turns to allow images to be formed from different angles. For example the person may face back wall 120 for an image of the back of the person to be formed. Images may also be formed with a person's sides facing the camera.

If the inspection system detects contraband carried on, under or inside the clothing of the person, an indication of the location of the contraband will be presented to an operator through operator interface 112. Where the system indicates contraband, the person may be denied passage through the checkpoint, searched or otherwise subject to other security screening. Information presented on operator interface 112 may guide the search, with the search starting in the area indicated to contain contraband, with a more complete body search being done second, if necessary or desirable. Alternatively, some other appropriate action may be taken, such as denying the person access to specific locations. The appropriate action taken in response to indications that people have concealed weapons or other contraband on their persons will depend on the intended use of the inspection system. Also, it is not necessary that images be presented to a human operator. Decisions about whether a person has concealed contraband may be made by a computer programmed to apply threat detection algorithms to the images obtained by inspection system 100.

Figure 2A:
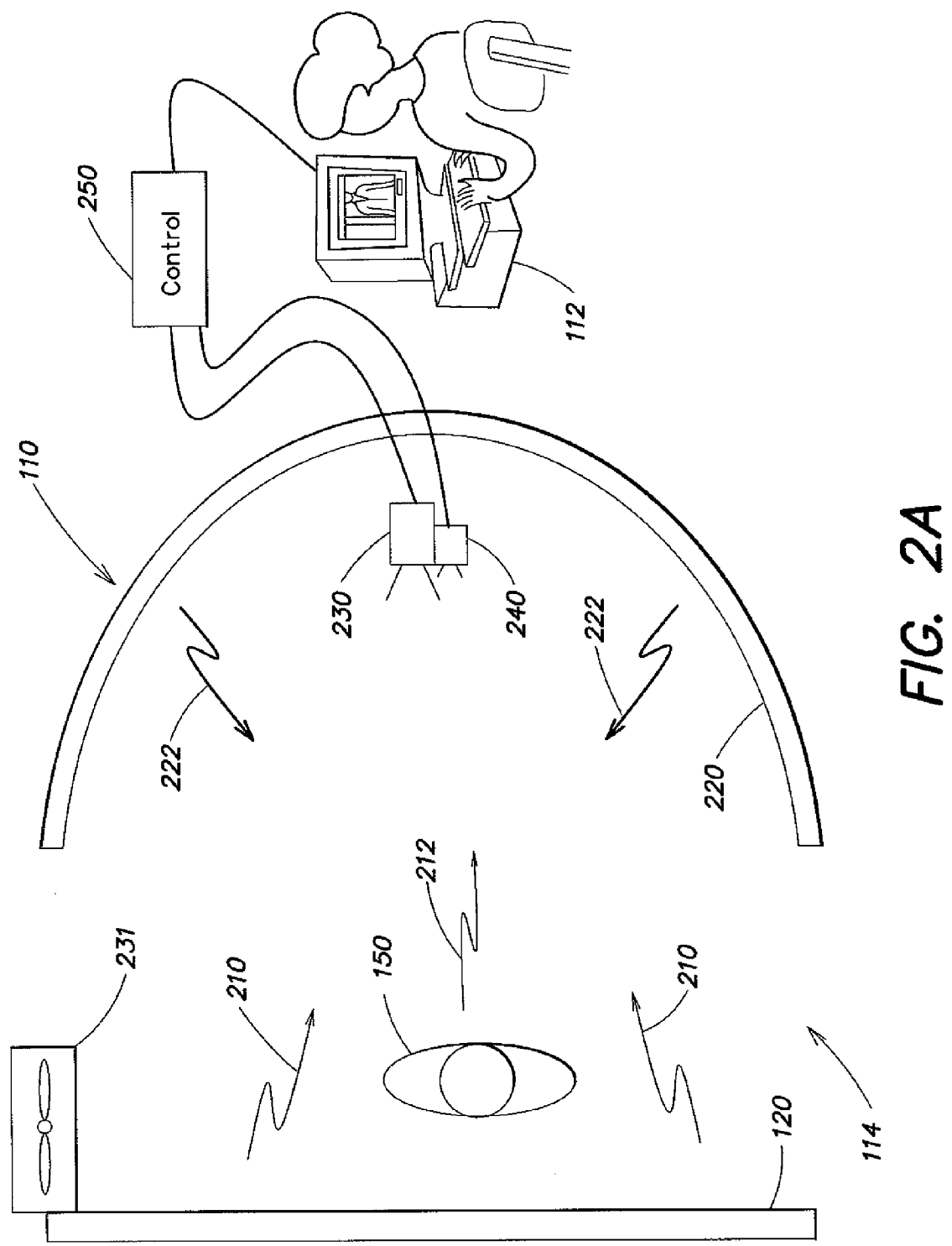
FIG. 2A is a top view of the inspection system of FIG. 1 when no contraband is present.

FIG. 2A shows the inspection system 100 in an alternative view useful in understanding its operation. Portal 110 is shown in a top view such as may be seen if the roof of portal 110 were removed. Portal 110 is one example of a mechanism that could be employed to increase the contrast between a person and a contraband item. In the view in FIG. 2A, a person 150 is standing against back wall 120. The person is shown facing two cameras numbered 230 and 240. In one embodiment, camera 230 is a millimeter wave camera and camera 240 forms a visual image of the person. Preferably, cameras 230 and 240 are coupled such that the images formed with each camera can be spatially correlated.

In one embodiment, camera 240 forms an image of person 150 using visible light. However, a camera forming an image using infrared or other relatively short wavelength radiation may be used. Preferably, camera 240 forms a relatively high resolution image and may be, for example, a conventional CCD video camera. Camera 230 may be a millimeter wave imaging camera that takes radiometric samples of the passive millimeter wave radiation emanating over the spatial extent of the objects which it images. Millimeter wave refers generally to radiation that has a frequency between approximately 20 and 300 GHz (gigahertz). In one embodiment, camera 230 is sensitive to frequencies in a relatively narrow band of the millimeter wave spectrum. Preferably, camera 230 will be sensitive to either one band or more than one band of a band of frequencies somewhere in the range between approximately 20 GHz and 300 GHz. In one embodiment, camera 230 will operate in a band spanning some or all of the frequency spectrum between 90 GHz and 140 GHz. For example, camera 230 may be a 94 GHz millimeter wave imaging camera, with an instantaneous bandwidth of approximately 6 GHz, or camera 230 may have a plurality of radiometric receivers operating in discrete bands that are each about 6 GHz wide and where each receiver is centered at 3 to 5 discrete center frequencies between 20 and 300 GHz. For example, bands encompassing one or more of the frequencies 35 GHz, 94 GHz, 140 GHz and 220 GHz may be used.

Millimeter waves have relatively long wavelengths. Images formed with radiation of relatively long wavelength are inherently lower resolution than images formed with shorter wavelengths. The spatial resolution of millimeter wavelength images can be improved by increasing the diameter of the millimeter wave antenna used within the camera, but for practical implementations, the spatial resolution of the millimeter wave camera is relatively coarse as compared to a visible image taken with a standard video camera. Camera 230 has a spatial resolution lower than that of camera 240. For example, camera 230 may have a resolution of approximately one centimeter and form images containing approximately one thousand pixels. In contrast, camera 240 may form images with the resolution 2-3 orders of magnitude greater than camera 230.

Images formed by both cameras 230 and 240 are provided to a control system 250. Control system 250 is a computer data processing system, such as are widely used in inspection systems. In the illustrated embodiment, control system 250 processes the image data provided by camera 230, though the data may be processed in hardware located in any convenient spot and connected to portal 110 through a network. In processing the image data, control system 250 runs algorithms to detect whether person 150 is carrying contraband. Camera 230 and control system 250 may operate with one radiometric camera band or a plurality of radiometric camera bands over the range from 20 to 300 GHz. Several camera bands may be used simultaneously by the algorithms to enhance detection of certain types of contraband objects, or automatic threat detection algorithms may use data collected in certain bands to identify contraband objects that have material properties such that they emit or reflect relatively large amounts of radiation in that band.

If contraband is detected, an indication is provided at operator station 112. A visible image formed by camera 240 is displayed on the operator station 112. Overlayed on this visible image is an indication of contraband identified in the image formed by camera 230. Because the images formed by camera 230 and 240 can be related spatially, the position of the contraband detected from an image formed by camera 230 can be related to the image formed by camera 240.

In the example shown in FIG. 2A, person 150 is not carrying any contraband. Thus, no indication of contraband exists in the image formed from camera 230. Inspection system 100 operates by detecting Blackbody radiation with a signature characteristic of contraband. It is known that all objects emit small amounts of Blackbody radiation. The amount of power radiated is proportional to the physical temperature of the object as well as the object's camera band emissivity and reflectivity. This radiation is in a frequency band or bands that is detected by millimeter wave camera 230. Thus, the image formed by camera 230 represents a picture of Blackbody radiation and can be formed without any active illumination of person 150 or the surrounding environment using a powered microwave or millimeter wave transmitter device of any type. However, the physical temperature of the surroundings may be adjusted so that the natural blackbody radiation near the person is optimized for detection of contraband objects on the person.

FIG. 2A shows radiation 212 being emitted from various spatial locations on the person 150. Blackbody radiation in the millimeter wave bands continuously emanates from all natural and cultural objects and the strength of the Blackbody Radiation in each case depends upon the physical temperature of the object as well as the object's specific emissivity and reflectivity at each frequency being measured. In the illustrated embodiment, back wall 120 is designed to radiate its Blackbody radiation with characteristics similar to the Blackbody radiation emitted by person 150. As will be described in greater detail below, back wall 120 can be made to radiate similarly to a person 150 by setting the physical temperature, reflectivity and emissivity of back wall 120 to be similar to the Blackbody radiating characteristics of person 150.

FIG. 2A shows radiation 210 emanating from wall 120 and radiation 212 emanating from the person 150. Because the person and back wall have temperatures for Blackbody radiation purposes that are roughly equivalent, the radiation 210 and 212 has substantially the same properties. Thus, while video camera 240 can form an image of person 150, millimeter wave camera 230, which is sensitive to radiation in the frequency band of radiation 210 and 212, does not detect a significant difference between radiation from person 150 and radiation for back wall 120 when different spatial regions located on or near the individual being imaged are measured with millimeter wave camera 230. In this scenario, little or no information appears in the image formed by camera 230. Preferably, processor 250 is programmed to ignore regions that have Blackbody Radiation signatures that are substantially similar to the signature that is seen by the millimeter wave camera when viewing the individual without contraband objects.

FIG. 2A shows that the front wall of portal 110 emits radiation 222. In the illustrated embodiment, front wall 220 is maintained at a temperature that is different than back wall 120. Therefore, radiation 222 will have a different peak intensity than radiation 210. In one embodiment, front wall 220 is maintained at a temperature that is elevated relative to back wall 120 and person 150. For example, front wall 220 may be maintained at a temperature in the range of 130 to 150 degrees Fahrenheit. In this case, the radiation from front wall 220 has a higher Blackbody temperature than the radiation from back wall 120.

Despite the fact that front wall 220 is emitting radiation 222 which can interact with person 150 or back wall 120, radiation 222 does not have a significant effect on the image formed by camera 230. Back wall 120 includes materials that absorb millimeter wave radiation. Thus, any radiation 222 reflected back to camera 230 is of very low intensity. Though radiation 222 has a higher peak intensity than radiation 210 or 212, the intensity of radiation 222 is so low in absolute terms that it has no significant effect on the temperature of person 150 or back wall 120 when absorbed.

As will be described below, back wall 120 and front wall 220 are in some embodiments heated to produce radiation at a Blackbody temperature in excess of 90 degrees Fahrenheit. However, as will be described below, the walls are constructed such that heating of the walls does not significantly increase the air temperature inside portal 110. Further, portal 110 can be built to include an air circulation system, such as is illustrated by fan 231. A ventilation system can be used to control the environment experienced by the person 150 within portal 110 to maintain it at a temperature that is below the Blackbody radiating temperatures of the walls. The temperature of the air inside the booth need not be the same as the internal temperature of the walls, which determines the amount of Blackbody radiation emitted.

Figure 2B:
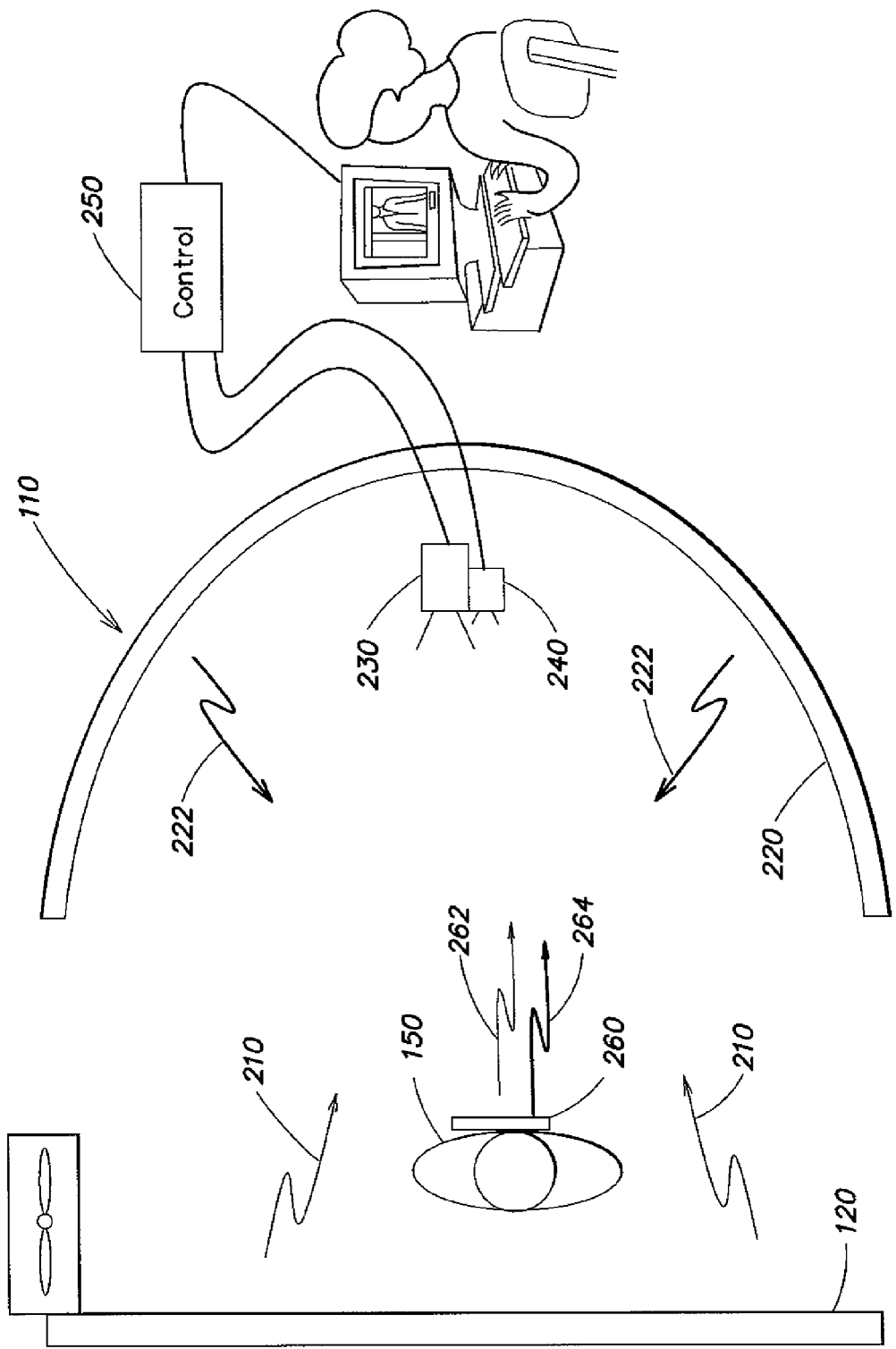
FIG. 2B is a top view of the inspection system of FIG. 1 when contraband is present.

FIG. 2B shows portal 110 configured as in FIG. 2A. However, FIG. 2B differs in that person 150 has concealed an object 260 beneath his clothes. Object 260 has substantially different emissivity and reflectivity than the emissivity and reflectivity of the person. As in the case of FIG. 2A, person 150 and back wall 120 have similar emissivity and reflectivity so that their Blackbody radiation is at approximately the same temperature. Therefore, person 150 is not readily visible in the image formed by millimeter wave camera 230. Concealed object 260, if it is carried in, on or below the clothing on a person, is likely at to be approximately the same physical temperature as the person. Therefore, if concealed object 260 had roughly the same emissivity and reflectivity as the person, it would produce radiation illustrated at 262 having roughly the same temperature as radiation produced by person 150 and back wall 120. Radiation at this temperature is illustrated by radiation 262. However, most contraband objects do not have the same emissivity and reflectivity as the person, and such contraband objects typically have much higher reflectivity and much smaller emissivity than the person, or they have much higher emissivity and much lower reflectivity than the person. For this reason, concealed object 260 can be detected in an image formed by millimeter wave camera 230. If concealed object 260 has higher reflectivity and a lower emissivity than the person, it reflects the more intense radiation from front wall 220. If concealed object 260 has higher emissivity and lower reflectivity than person 150 it reflects very little incident radiation and radiates at or near to physical temperature and appears at a lower relative temperature than the person when viewed by the camera. Certain contraband objects such as metals or ceramics have a very high reflection coefficient in the millimeter wave spectrum. Other forms of contraband, such as explosives, may either have a higher or lower reflection coefficient depending upon the chemical composition of the explosive, when compared to the reflection coefficient of person 150. Yet other types of contraband have surfaces that only appear to absorb radiation and have low reflectivity and high emissivity and appear at a lower temperature than the person when viewed by the camera. In some embodiments, the algorithms in control computer 250 will be capable of discriminating between objects that are reflective and absorptive so as to further assist in classifying the type of object being scanned.

Radiation such as 222 emanating from front wall 220 reflects from concealed object 260, such as is illustrated by radiation 264. The radiation from concealed object 260 will be a combination of radiation 262 and 264. Radiation 264 will be at a measurably different Blackbody temperature than radiation from person 150 and back wall 120. Thus, even if person 150 does not appear in an image formed by camera 230, contraband objects carried on the person 150 will appear in the image.

The appearance of objects in the image formed by millimeter wave camera 230 can be used as an indication of contraband objects concealed on person 150. Even if the object 260 is obscured by clothing on person 150, camera 230 may still detect radiation 264 from object 260. Clothes normally worn by people tend not to either reflect or attenuate millimeter waves except by a small amount and therefore have almost no effect on the image formed by camera 230.

Figure 3B:
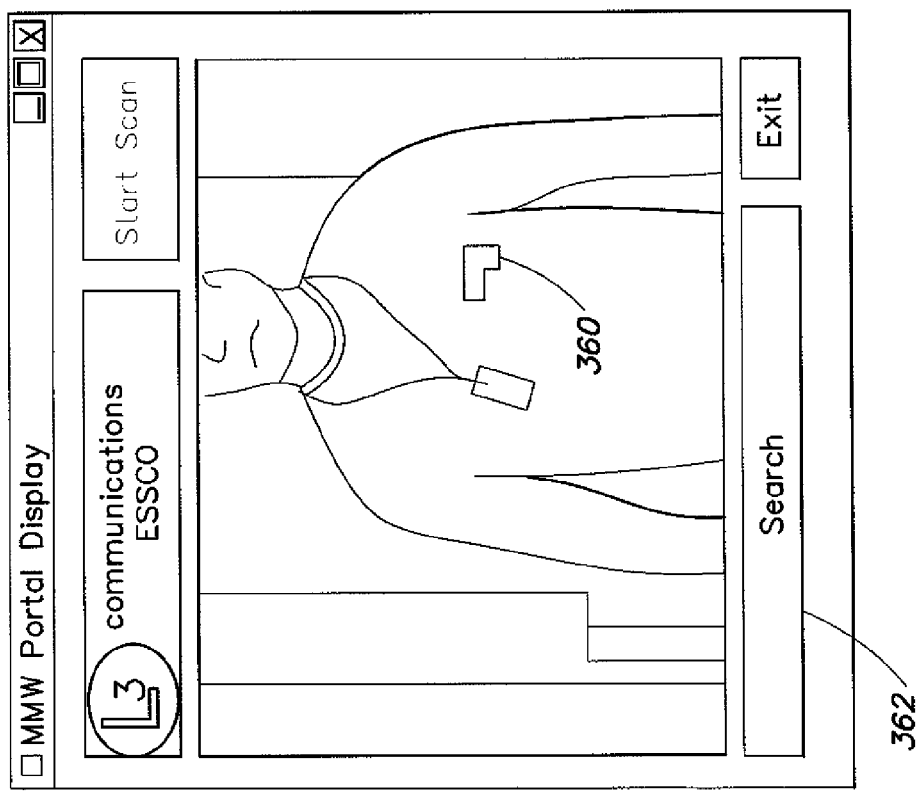
FIG. 3B is an illustration of an operator display when contraband is present.
Figure 3A:
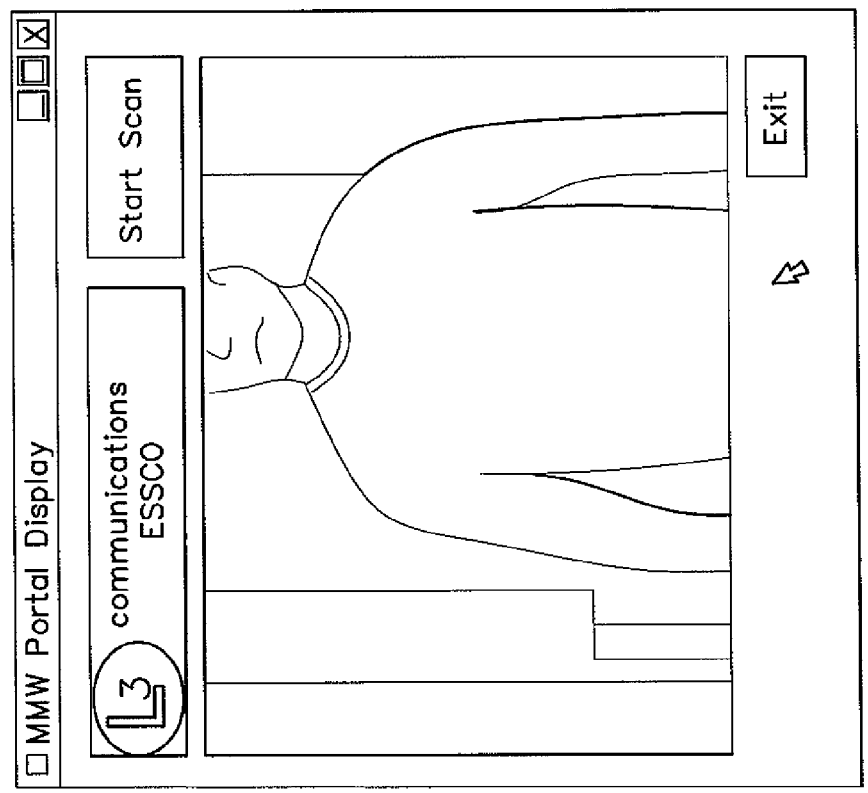
FIG. 3A is an illustration of an operator display when no contraband is present.

FIGS. 3A and 3B illustrate how images formed by cameras 240 and 230 may be processed by controller 250 to present an image useful in detection of concealed contraband. FIGS. 3A and 3B show the superposition of images formed by cameras 230 and 240. In the scenario of FIG. 2A, camera 230 detects radiation from back wall 120 and person 150, which is in the dead zone. The dead zone is implemented by an image processing algorithm within controller 250 that removes from the image formed by camera 230 what is effectively background noise for the detection of contraband. In this case, the controller is programmed to ignore blackbody radiation representative of what may be emitted by back wall 120 or a person 150 at normal body temperature. Because in the scenario of FIG. 2A, all the radiation from back wall 120 and person 150 falls in the dead zone, camera 230 effectively forms a blank image. When the blank image formed by camera 230 is superimposed with the image formed by camera 240, the result is effectively a video image such as may be formed by camera 240 alone. This image is illustrated in FIG. 3A.

The system preferably does not directly display images of a person formed from a mm wave camera scan. Doing so creates privacy concerns. Because the mm wave camera effectively "sees through" clothes, an image formed with the mm wave camera resembles a picture of a person taken without clothes. Thus, detecting contraband in a mm wave image but displaying an indication of the contraband in connection with a visible light image addresses potential privacy concerns as well as presenting the information in a format readily understandable to the human operator of the inspection system.

In the scenario shown in FIG. 2B, contraband item 260 causes camera 230 to detect radiation outside the dead zone. Accordingly contraband item 260 appears in the image formed by millimeter wave camera 230. When the images formed by cameras 230 and 240, are overlaid, the contraband item appears in the image such as is illustrated in FIG. 3B.

FIG. 3B illustrates the operator interface that may be presented when an object appears in the image formed by camera 230. For example, items appearing in the image formed by camera 230 may be presented in the image as brightly colored regions such as 360. The regions may, for example, be red or other highly noticeable color.

Image processing algorithms may be used to filter the images formed by camera 230 such that only items in the image of sufficient size to represent contraband items appear in the image. In addition, boundary detection algorithms may be applied to the image formed by camera 230 to highlight objects such as contraband 260. Further, region identification algorithms may be employed to better distinguish between contraband items imaged by camera 230 and image effects or noise. Further image processing may be applied. For example, object or shape recognition algorithms may be applied to further increase the probability that pixels in the image are actually the result of items carried by person 150. Furthermore, multiple decision surfaces based upon evaluations in a plurality of camera bands may be used to form a final decision surface. This procedure would further enhance detection probability and decrease false alarm rate.

Controller 250 may also include automatic object detection algorithms. In one contemplated embodiment, if controller 250 detects an object within the millimeter wave image formed by camera 230, it will signal to an operator that person 150 needs to be searched to verify whether the person was carrying concealed contraband. When controller 250 detects in the image formed by camera 230 an object that could represent a weapon or other contraband, it will cause a search indicator to appear on the operator interface. FIG. 3B illustrates a search bar 362 that may be displayed on the operator interface. The search bar or some equivalent screen display artifact may blink or otherwise take on properties intended to attract an operator's attention. Alternatively, an alarm can be given in audible form or in any other convenient manner.

Figure 4:
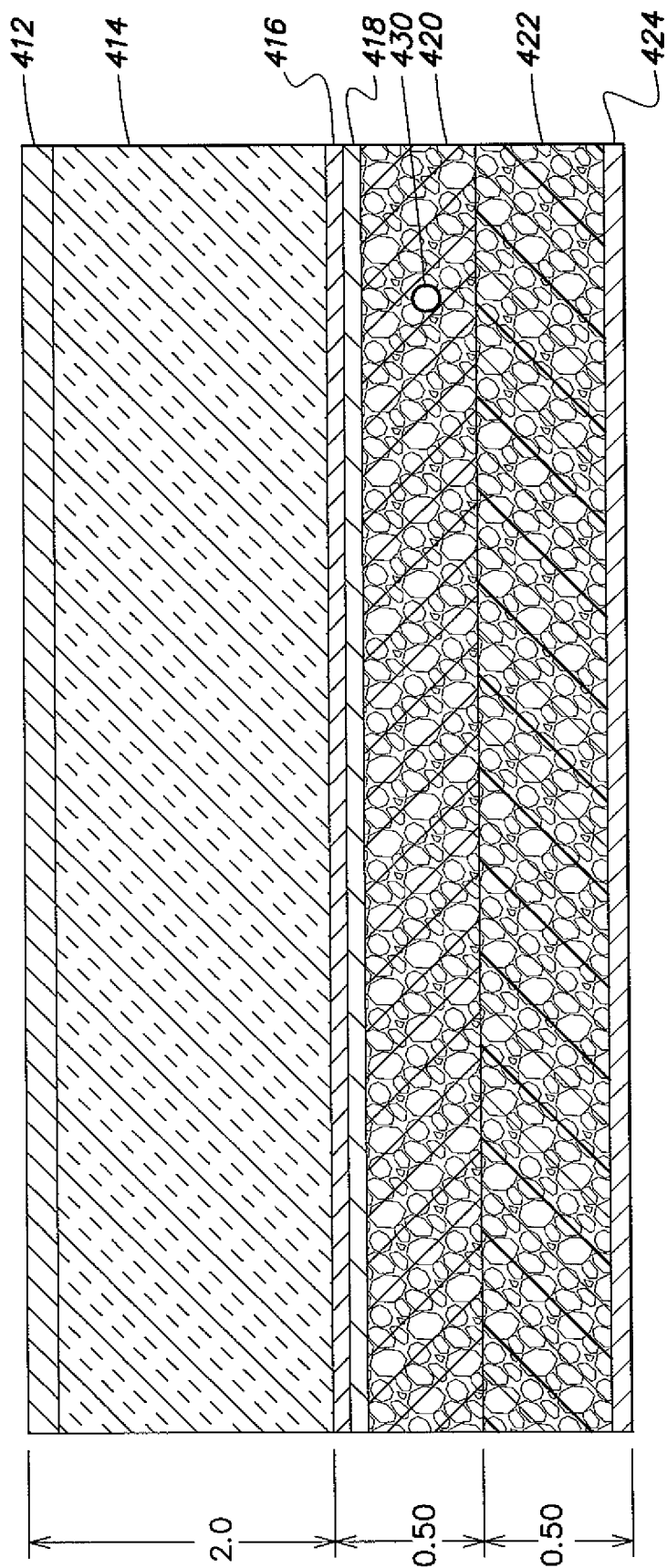
FIG. 4 is a cross-sectional view of an embodiment of a wall of the inspection portal of FIG. 1.

Turning to FIG. 4, a cross sectional view of one of the walls of portal 110, such as back wall 120, is shown. As described above, it is desirable that the walls of portal 110 emit Blackbody radiation that is either a lower or higher temperature than that of the person. However, it is desirable that the design of the portal not modify the ambient temperature in the area inside the portal 110 or allow the walls of the portal to drop below the dew point of the local ambient air at any time. FIG. 4 shows a suitable wall structure.

The wall may include a structural member as a base. In FIG. 4, a structural aluminum outer wall 412 is illustrated. The base member is relatively thin and may for example be a 1/32" thick sheet of aluminum.

A thermally insulative material is attached to the base member. In FIG. 4 the insulative material is shown as polystyrene insulation 414. In embodiments where the wall is operated at an elevated temperature, polystyrene thermal insulation layer 414 keeps the rear surface of the wall from feeling hot.

In the embodiment shown in FIG. 4 the wall includes a heating element. Here, a commercially available resistive heating blanket 416 is used. The heating blanket is a layer of resistive heating elements disposed on a flexible substrate. By increasing or decreasing the amount of electrical power supplied to the heating blanket, its temperature can be regulated.

A heat spreader 418 may optionally be used in connection with heating blanket 416. Heat spreader 418 is a sheet of material that has high thermal conductivity, such as an aluminum sheet. The heat spreader will be at a relatively uniform temperature even if heating blanket 416 heats unevenly such that some portions of heating blanket 416 are hotter than others.

The wall also includes a region of material that will absorb millimeter waves in the frequency range which camera 230 may detect. Absorber material 420 may, for example, be a carbon-loaded foam or a reticulated foam absorber material. Any stray millimeter wave radiation from nearby natural or cultural objects that is at a higher or lower Blackbody temperature than the physical temperature of the absorber in the wall will be absorbed into absorber material 420. The absorber then radiates Blackbody radiation proportional to its physical temperature irrespective of the presence or absence of any stray millimeter radiation incident on the absorber.

To ensure that absorber material 420 radiates Blackbody radiation of the desired characteristics, its temperature is controlled. Thermal couple 430 is embedded in absorber material 420. If the temperature of layer 420 increases because of absorbed radiation, this increase will be sensed by thermal couple 430, which is connected in a feedback loop to heating blanket 416. The amount of power generated by heating blanket 416 will be decreased, keeping the temperature of absorber material 420 at the desired level. In the example where the rear wall 120 radiates at a Blackbody temperature of ninety degrees Fahrenheit, the feedback loop holds the temperature of absorber material layer 420 at ninety degrees Fahrenheit.

A layer of thermally insulative material is added over absorber material layer 420. In contrast to layer 414 which does not impact operation of the system if it absorbs mm wave radiation, insulative layer 420 is preferably transparent to mm wave radiation and does not absorb water. In one embodiment, the insulative layer may be layer 422 of closed cell urethane radome foam. Such a foam layer would provide relatively good thermal insulation but would be relatively transparent to millimeter waves.

A protective layer 424 can be placed over the urethane foam layer 422. A material such as is used to form coverings on radomes may, for example, be used. Preferably layer 424 is constructed from a low loss radome material that is transparent to radiation in the frequency range measured by camera 230 yet provides sufficient mechanical protection for the underlying structure of the wall.

Figure 5:
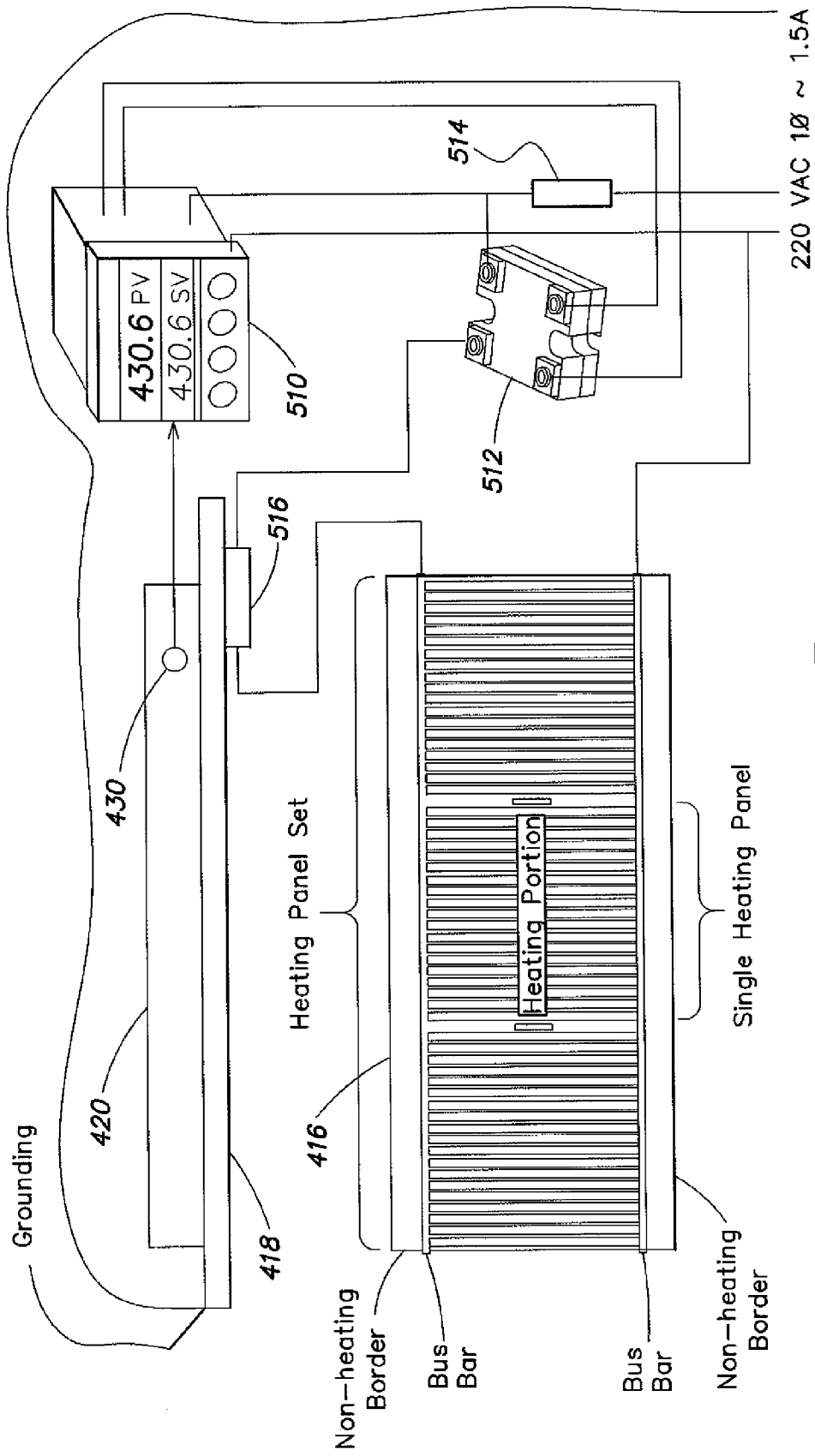
FIG. 5 is a sketch illustrating operation of the walls of the inspection portal of FIG. 1.

FIG. 5 shows the electrical components of the wall in schematic form. In this embodiment, a temperature controller 510 receives an input from thermal couple 430. Temperature controller 510 produces an output that will increase or decrease the power provided to heating blanket 416. In this way, absorber material 420 is maintained at the desired temperature.

Other elements such as are commonly found in electronic control systems may also be included. For example, a thermal cutout switch 516 may also be included. Thermal cutout switch 516 may prevent the wall from being heated to a temperature at which damage may occur. Likewise, a fuse 514 may be employed to prevent the system from drawing dangerous amounts of power. Also, solid state relay 512 takes low voltage control signals from Temperature Controller 510 and switches on and off the high current high voltage power that is being supplied to the heating blanket 416.

FIG. 5 also illustrates the structure of a commercially available heating blanket 416. Bus bars deliver power to resistive elements.

Figure 6:
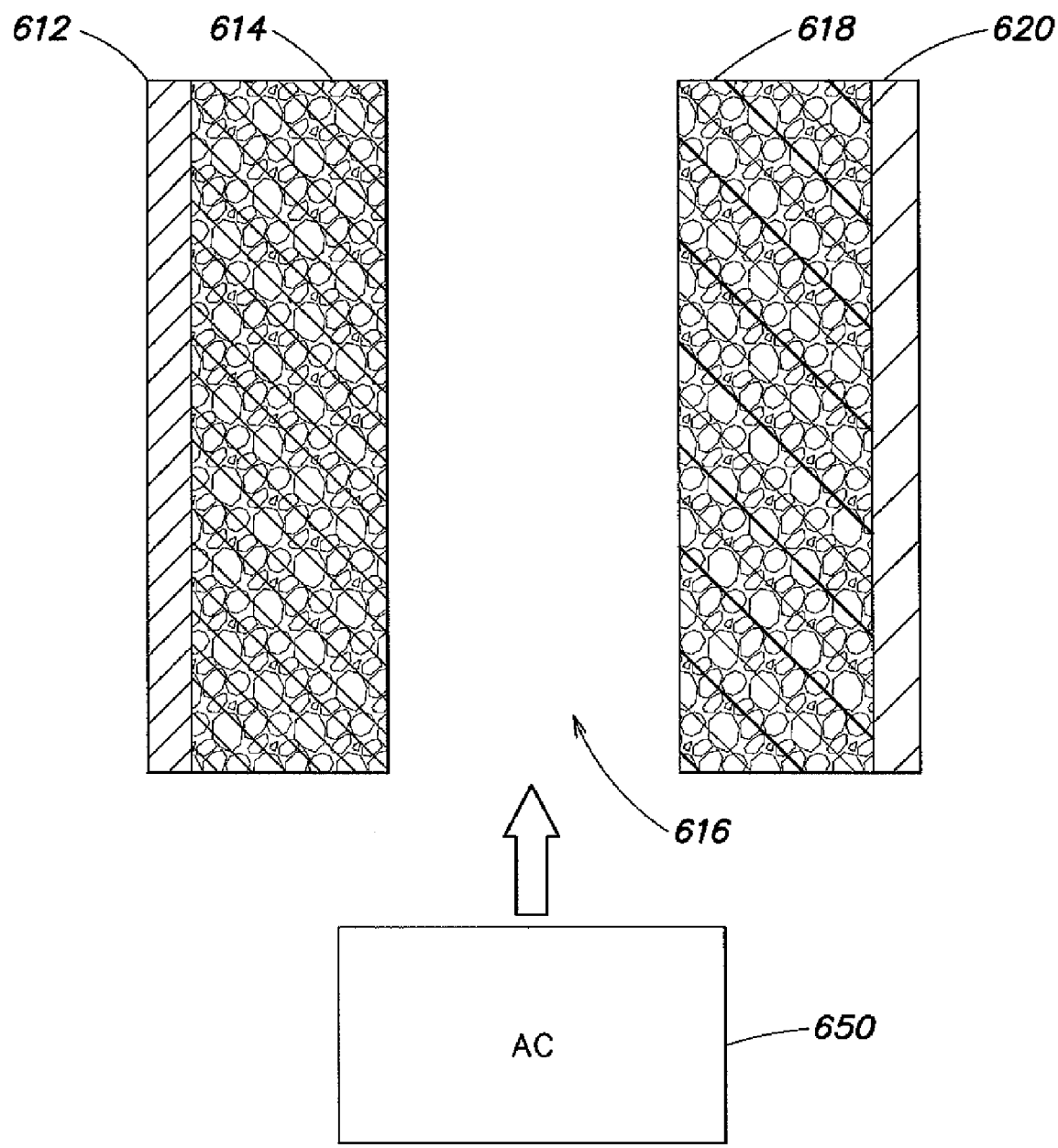
FIG. 6 is a sketch illustrating an alternative embodiment of the walls of the inspection portal of FIG. 1.

FIG. 6 shows an alternative wall construction. As described above, a temperature contrast is created between the wall behind person 150 and the surrounding environment. It is not necessary that the walls of portal 110 be heated. As an alternative, the wall may be cooled. FIG. 6 shows a wall structure that may be used when it is desired to cool the wall. The wall shown in FIG. 6 has an exterior aluminum skin 612 similar to aluminum skin 412 in the wall shown in FIG. 4. The wall in FIG. 6 has a layer of mm wave absorber 614, similar to the layer 420 in FIG. 4.

Rather than containing a source of heat with a heat spreader, the wall in FIG. 6 contains a plenum through which cold air may be circulated. When the wall such as shown in FIG. 6 is employed, a source of cold air, such as air conditioning unit 650, blows air into plenum 616. The flowing air provides both the means to cool the wall and spread the cooling evenly over the interior surface of the wall.

Any heat generated within absorber material 620 from absorbed radiation coming from natural or cultural objects is small and is easily dissipated by the cold air flowing through plenum 616, thereby maintaining absorber material 614 at a constant physical temperature. Absorber material 618 will produce Blackbody radiation in proportion to its physical temperature which is set by the temperature of the ambient air in the plenum.

Layer 618 may be thermally insulative foam that is preferably transparent to mm wave radiation. It may be similar to layer 422 in FIG. 4. The outer layer 620 is also preferably transparent to radiation. It may be similar to layer 424 in FIG. 4.

Figure 7:
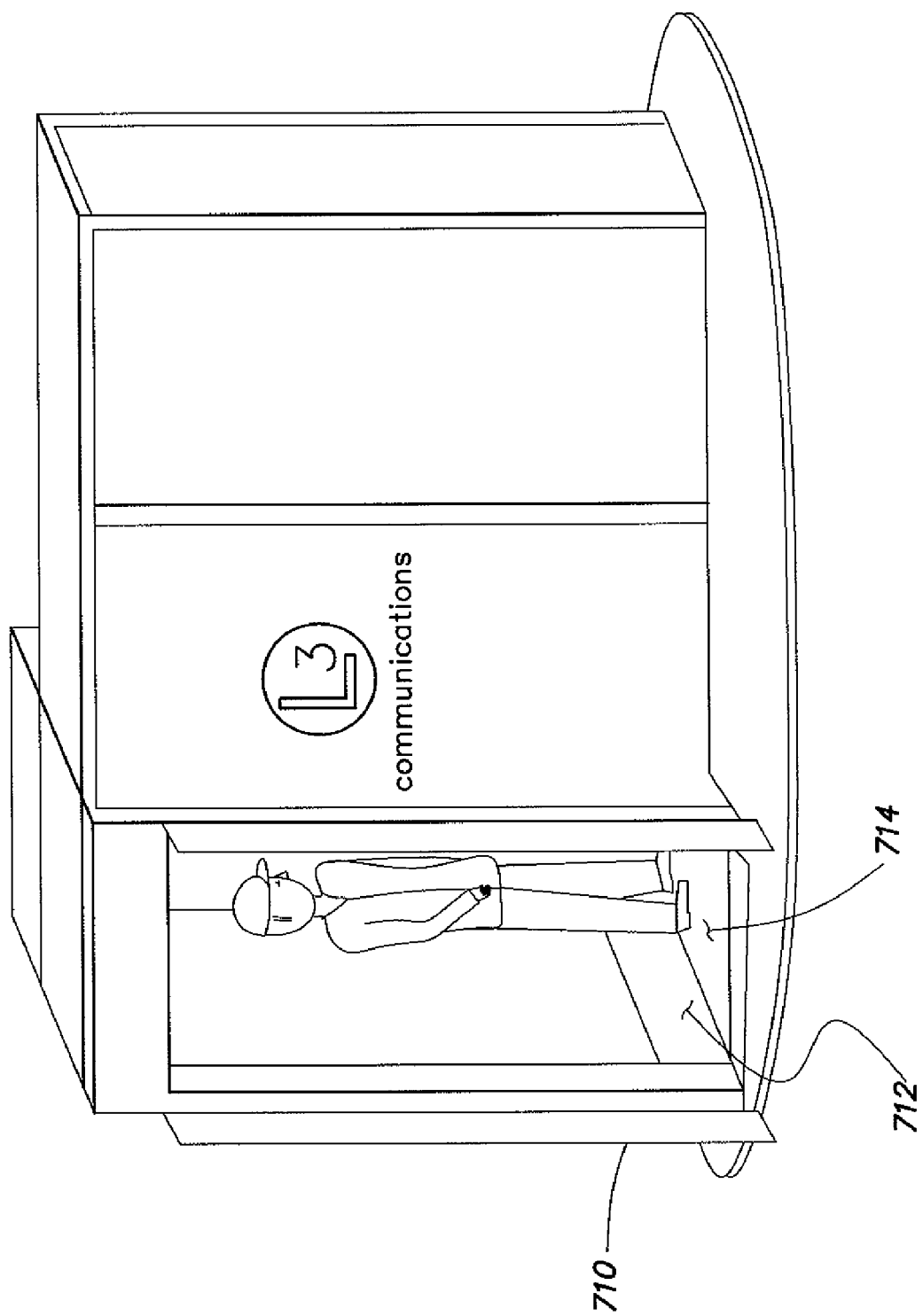
FIG. 7 is a sketch of an inspection system incorporated an orthogonal inspection technology.

FIG. 7 shows an alternative embodiment of an inspection system employing millimeter wave detection of concealed items. The system of FIG. 7 includes an inspection portal 110, which may be as described above. The entry way to portal 110 is equipped with a metal detector 710 such as is widely used at inspection stations. Using the millimeter wave inspection system in connection with an orthogonal inspection system increases the probability of detecting concealed weapons. FIG. 7 uses as an example a metal detector, but other forms of orthogonal technologies may be used. For example, terahertz sensors, chemical sensors or nuclear quadrupole resonance systems may alternatively be employed. Preferably, whatever orthogonal technology is used in conjunction with millimeter wave imaging will also be a passive imaging technology.

Figure 8:
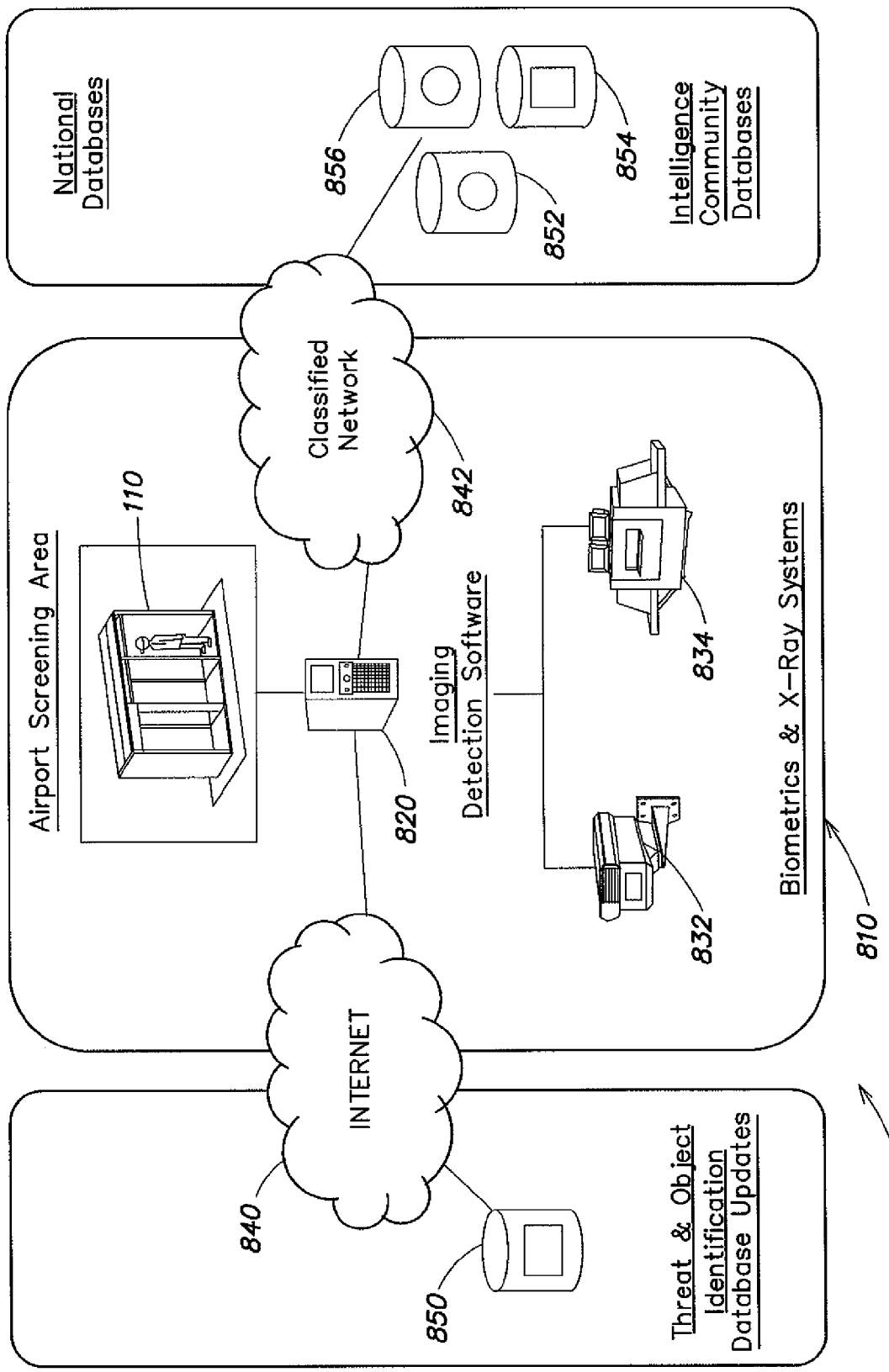
FIG. 8 is a block diagram of an integrated airport security system.

FIG. 8 illustrates an airport security system 800 in which an inspection portal such as 110 may be integrated. Portal 110 may be included in a screening area or security checkpoint 810. Data from inspection portal 110 may be provided to a computer 820. Computer 820 may be a computer integrated with an operator station such as 112 (FIG. 1) or may perform autonomously without human intervention.

In addition to receiving data from portal 110, computer 820 may receive information from other sources. In system 800, inspection area 810 may include a line scanner 834, such as may be used to inspect carry on baggage. In addition, inspection area 810 includes a biometric scanner 832. Biometric scanner 832 may, for example, be a video camera coupled to an automatic face recognition system.

Computer 820 may be programmed to synthesize data from various sources. Data may be synthesized relating to a specific passenger. When biometric data matches the person suspected of terrorist activity, the threshold settings for the other inspection systems may be decreased, such that even small quantities of suspicious materials would result in an alarm being triggered.

Data gathered from the mm wave inspection system within portal 110 may be combined with information from carryon baggage scanner 834 to increase the confidence that a particular passenger has no contraband items. For example, biometric information may be used to validate the identity of the passenger. For example, small quantities of material that could be an explosive but would normally be considered too small to trigger an alarm, may trigger an alarm if such small quantities were detected both by the carryon inspection and the mm wave inspection of the person. In addition, appropriate responses to suspicious items identified by the mm wave inspection system or the carryon baggage scanner 834 may be determined based on information derived from other sources.

In addition, inspection system 800 includes one or more network connections allowing the threat detection software running at computer 820 to either be updated or receive new data. For example, computer 820 is shown connected over a network, which may be the internet 840, to a threat and object identification database 850. Computer 820 may download information from database 850 as information is updated. Database 850 may contain programs that perform threat or object identification. Alternatively, database 850 may contain data indicating parameters or threshold levels that should be used by threat detection programs on computer 820.

In addition, computer 820 is shown connected over a network 842, which may be a classified network. Classified network 842 allows computer 820 access to intelligence databases such as 852, 854, and 856. These intelligence databases may include information about individuals suspected of terrorist activity or information about a general threat of terrorist activity. Computer 820 may use this information to adjust thresholds or otherwise alter its threat detection processing for specific conditions. For example, alarm thresholds may be set lower for any individual suspected of terrorist activity or for travelers boarding flights for which there is a threat of terrorist activity.

Figure 9:
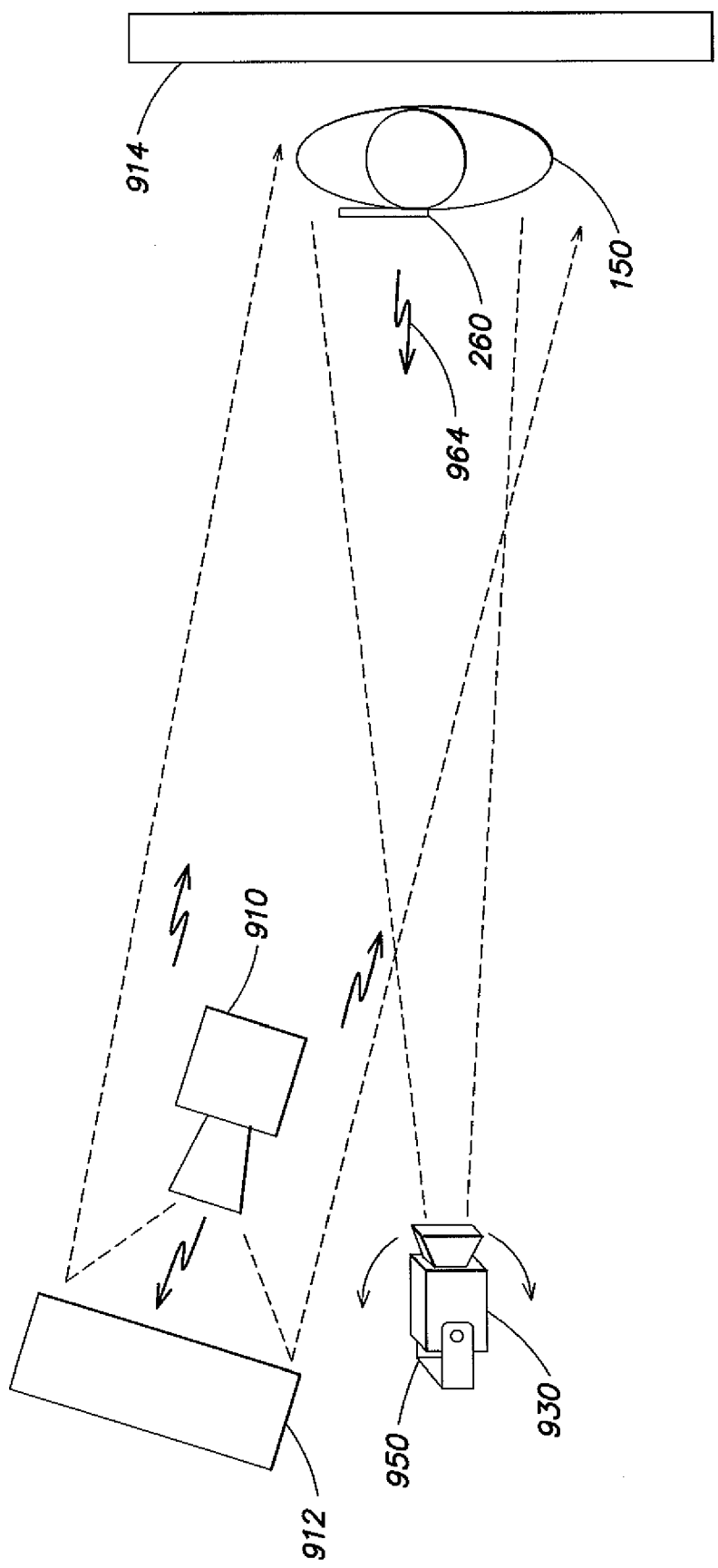
FIG. 9 is a schematic representation of an alternative embodiment of an inspection system.

FIG. 9 shows an alternative embodiment of a screening system in which a transmitter 910 is used to increase the contrast between a person 150 and a concealed object 260. Transmitter 910 may be a solid state noise transmitter outputting random or quasi-random noise over one or more of the bands to which camera 930 is sensitive.

In the system of FIG. 9, noise output by transmitter 910 is directed at spatial phase randomizer 912. Spatial phase randomizer 912 may be formed from a series of specially shaped plates and surfaces that act on the radiation from noise transmitter 910 to reflect a beam of radiation having a large number of random phases and amplitudes as a function of the spatial location over the field of view from camera 930. Concealed objects that reflect radiation from noise transmitter 910 will appear with much greater contrast in an image formed by camera 930 than a person 150, which will absorb much of the radiation from noise transmitter 910.

In the embodiment of FIG. 9, the person 150 is shown against a background 914. Background 914 may be a portion of an inspection portal such as 110. Alternatively, a system may be implemented in which no specific background 914 is used. For example, the system may be used to inspect people for contraband as they stand in line at airport ticket counters, check in stations or as they are otherwise occupied without requiring them to enter a specific inspection station. Camera 930 maybe a mm wave camera as described above in connection with camera 230. Camera 930 may have integrated with it a visual camera, such as camera 240.

In the illustrated embodiment, camera 930 is equipped with a mechanical translation device 950. Mechanical translation device 950 allows camera 930 to move relative to person 150. Mechanical translation device 950 may be used for bringing a person 150 within the field of view of camera 930, which will be particularly useful when the system is not used in connection with a fixed inspection station. In addition, mechanical translation device 950 allows camera 930 to scan its field of view over person 150. In this way, the field of view of camera 930 need not encompass the entirety of person 150. Camera 930 may have a field of view, for example, encompassing about one half of person 150. In this embodiment, camera 930 may take an image of a portion of the person 150 after which the field of view camera 930 would be changed by moving mechanical translation device 950 to reposition camera 930 with its field of view on a second portion of the person 150.

Mechanical translation device 950 may be a motor driven pivot mounting for camera 930 or any other suitable mechanism. In addition, it is not necessary that camera 930 be focused on different spots of person 950 through a mechanical translation device. For example, camera 930 may include a phased array of individual detectors that may be electronically steered to adjust the focal point of camera 930. Any suitable means for adjusting the focal point of camera 930 may be used.

Having thus described several aspects of at least one embodiment of this invention, it is to be appreciated various alterations, modifications, and improvements will readily occur to those skilled in the art. For example, to avoid the need to have a person turn around inside portal 110, an inspection portal may comprise two or more cameras, one to image the front, back and/or each side of the individual. Alternatively, the effect of two cameras may be simulated with a reflector behind the person or by use of reflectors and vertical translation of the scanning camera with a mechanical translation device.

Figure 10:
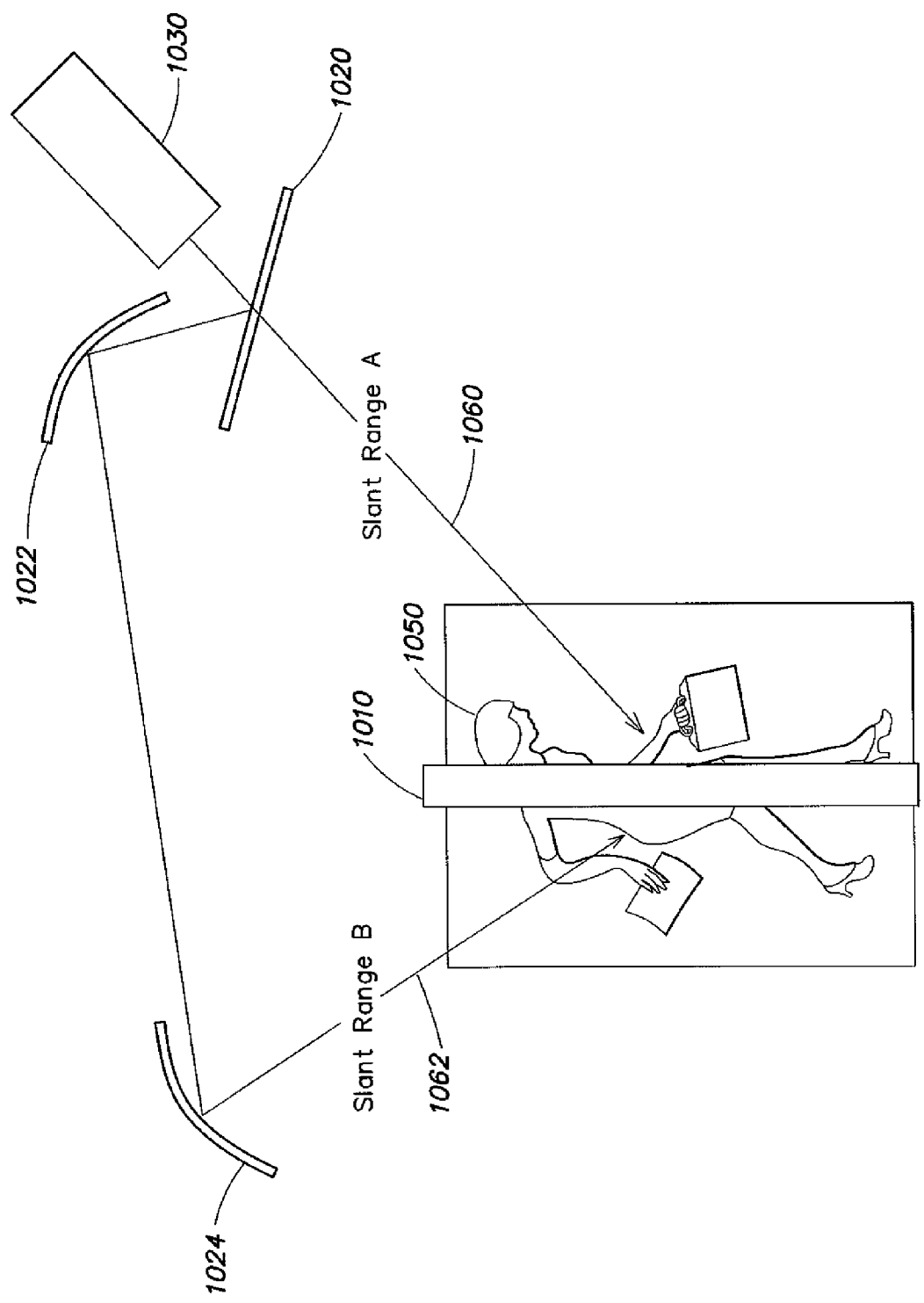
FIG. 10 is a sketch illustrating an alternative embodiment of an inspection system.

For example, FIG. 10 shows a system in which a single camera is used to image the front and back of a person. FIG. 10 shows a person 1050 passing through a portal 1010, which may, for example, be a metal detector as is traditionally used at security checkpoints. A camera 1030 is mounted relative to portal 1010 in any suitable manner. Camera 1030 may be a mm wave camera such as 930 or 230 as described above. Camera 1030 may also include a noise source such as 910 and/or a spatial phase randomizer 912.

Camera 1030 is mounted relative to a quasi-optic beam splitter 1020. Quasi-optic beam splitter 1060 allows a beam such as 1060 to pass straight through to camera 1030. Beam 1060 represents radiation to or from the front of person 1050.

In addition, quasi-optic beam splitter 1020 reflects radiation towards mirror 1022. Mirror 1022 is focused on a second mirror 1024, which directs a beam 1060 to or from the back of a person 1050.

In the embodiment illustrated, radiation from the front of a person 1050 and the back of a person 1050 is both provided to camera 1030 at the same time. Processing in camera 1030 may separate out the radiation 1060 from the radiation 1062 to create separate images of the front or back of person 1050. For example, radiation 1060 travels along a shorter path than radiation 1062. Accordingly, the range between camera 1030 and the front of person 1050 is shorter than the range between camera 1030 and the back of person 1050. Techniques that sort image signals based on the range between the detector and the object are known. For example, the received signal may be processed using a fast fourier transform or similar transformation. The signal bins created by the fast fourier transform can be taken to be representative of range.

In addition, other techniques for forming images of the front of a person and the back of a person using the same camera may be employed. For example, camera 1030 may directly face mirror 1022, which may be movably mounted. By rotating mirror 1022, camera 1030 could be effectively focused either at the front of a person 1050 or at mirror 1024, resulting in an image of the back of a person 1050 being formed.

Quasi-optic beam splitters such as 1020 and mirrors such as 1022 and 1024 are known. Preferably, the structures are formed from materials that have the desired properties in the frequency range in which camera 1030 operates. For example, in the 94 GHz band, a mirror can be created by placing a metal coating over a substrate such as plastic.

Further, the portal need not be constructed with directly opposing openings. The path through the inspection portal may make various turns so that when a person is being imaged by a camera, the appropriate background for an image is provided.

Furthermore, the camera need not be pointing directly at the individual. Reflectors may be used to divert radiation from the person to the camera. Using reflectors could reduce the overall size of the inspection portal. For example, FIG. 2A shows camera 230 spaced from person 150 a sufficient distance to capture the entire image of person 150 on the focal plane array in camera 230. If the camera is placed behind the person and a reflector in front of the person, diverting radiation to the camera, the spacing between the person and the reflector needs to be approximately one half the spacing between the camera and the person shown in FIG. 2A.

Alternatively, it is not required that camera 230 form an image of an entire person simultaneously. Camera 230 may scan person 150. In the extreme, camera 230 need not form a 2 dimensional image. It may more simply be a detector.

Also, it is not required that all of the walls be made to radiate at a particular temperature. Preferably, those portions of a wall that appear in an image will appear to have the same temperature. But, this result may be achieved by using reflective surfaces reflecting radiation from an object at the desired temperature. For example, FIG. 7 shows a metal band 712 at the bottom of wall 120. Portal 110 is shown to have a metal floor 714. If metal band 712 is not in the field of view of camera 230, the fact that it is reflective does not alter the performance of the system. Some portion of floor 714 may appear in the field of view of camera 230. To avoid reflections from floor 714 creating a false indication of contraband, the roof of portal 110 may be made similarly to walls 120. Thus, a floor 714 will appear in images formed by cameral 230 the same as back wall 120. Because floor 714 appears in the dead zone of the system, it will not impact contraband detection.

According, while specific materials and positional relationships are described, alternative materials and orientations are possible that create the appearance that all portions of the portal in the field of view of the millimeter wave camera are in the dead zone.

Further it was described that contrast between a person and a contraband item was created by surrounding the person and contraband with a wall that radiates with controlled characteristics. A similar effect may be achieved computationally using additional types of automatic target recognition algorithms without the need to actually control the foreground radiation. As one alternative, in place of a wall such as 220 to control the foreground radiation, incoming radiation may be measured and/or characterized. The same approach may be used in place of a wall 120. The background radiation may be measured and/or characterized. Systems may be employed with active and/or passive illumination of people or other objects to be inspected. For example, FIG. 2A shows contrast enhanced with passive radiation from a controlled surrounding. FIG. 9 shows a system in which radiation is specifically injected into the inspection area. Ambient radiation may also be used for illumination of the item to be inspected or active illumination may be used for objects not in controlled surroundings.

Also, the system of FIG. 2A is shown to include an optical camera in connection with a mm wave camera. Such a system alleviates privacy concerns associated with displaying mm wave images of people. Though no optical camera is shown in the system of FIGS. 9 and 10, such systems may be used with optical cameras to create operator display such as are shown in FIGS. 3A and 3B.

Also, it was described that an operator display is created by superimposing information from a mm wave image onto a visual image. The information from the mm wave image may be, but need not be, in the same shape as the actual contraband item. The contraband item may be represented as a rectangle or some other convenient shape. Also, it is not necessary that the visible image be formed with visible light. It may, for example, be formed using infrared radiation or may be the silhouette of the person.

Such alterations, modifications, and improvements are intended to be part of this disclosure, and are intended to be within the spirit and scope of the invention. Accordingly, the foregoing description and drawings are by way of example only.

The invention claimed is:

1. A contraband detection system, comprising:
    a) a first camera having a first field of view, the first camera having an output providing first image data representative of radiation in a first frequency band from items in the first field of view, wherein the first frequency band comprises visible light frequencies;
    b) a second camera having a second field of view at least partially overlapping the first field of view, the second camera having an output providing second image data representative of radiation in a second frequency band, the second frequency band being different from the first frequency band and comprising frequencies between 20 GHz and 300 GHz, the radiation in the second frequency band being representative of items in the second field of view; and
    c) a display station coupled to the first camera and the second camera to receive the first image data and the second image data, the display station comprising at least one computer programmed to present a display of items in the first field of view using the first image data selectively overlaid with an indication of at least one item derived from the second image data.

2. The contraband detection system of claim 1 wherein the first frequency band consists essentially of frequencies with shorter wavelengths than the frequencies in the second frequency band.

3. The contraband detection system of claim 1 additionally comprising a surface reflective of radiation in the second frequency band in the field of view of the second camera.

4. The contraband detection system of claim 1 additionally comprising an enclosure defining an interior space and wherein the first camera and the second camera are disposed in the interior space.

5. The contraband detection system of claim 4 wherein the enclosure comprises temperature controlled walls.

6. The contraband detection system of claim 5 wherein the temperature controlled walls comprise internally heated walls.

7. The contraband detection system of claim 5 additionally comprising a fan positioned to exchange air between the interior space and ambient environment.

8. The contraband detection system of claim 5 wherein the enclosure has at least one opening therein, each of the at least one openings being sized to permit a person to pass therethrough.

9. The contraband detection system of claim 8 additionally comprising a metal detector mounted adjacent an opening in the enclosure.

10. The contraband detection system of claim 8 wherein the at least one opening comprises at least a first opening and a second opening, with the second opening positioned opposite the first opening.

11. A contraband detection system, comprising:
 a) a first camera having a first field of view, the first camera having an output providing first image data representative of radiation in a first frequency band from items in the first field of view;
 b) a second camera having a second field of view at least partially overlapping the first field of view, the second camera having an output providing second image data representative of radiation in a second frequency band, different from the first frequency band, representative of items in the second field of view;
 c) a display station coupled to the first camera and the second camera to receive the first image data and the second image data, the display station comprising at least one computer programmed to present a display of items in the first field of view using the first image data selectively overlaid with an indication of at least one item derived from the second image data; and
 d) a transmitter transmitting millimeter wave radiation directed at the field of view of the second camera.

12. The contraband detection system of claim 11 wherein the transmitter comprises a noise-like illumination.

13. The contraband detection system of claim 11 wherein the transmitter additionally comprises a spatial phase randomizer.

14. A contraband detection system, comprising:
 a) a first camera having a first field of view, the first camera having an output providing first image data representative of radiation in a first frequency band from items in the first field of view;
 b) a second camera having a second field of view at least partially overlapping the first field of view, the second camera having an output providing second image data representative of radiation in a second frequency band, different from the first frequency band, representative of items in the second field of view; and
 c) a display station coupled to the first camera and the second camera to receive the first image data and the second image data, the display station comprising at least one computer programmed to present a display of items in the first field of view using the first image data selectively overlaid with an indication of at least one item derived from the second image data, wherein the first image data comprises a representation of objects in the first field of view with a first resolution and the second image data comprises a representation of objects in the second field of view with a second resolution and the first resolution is at least ten times greater than the second resolution.

15. The contraband detection system of claim 14 wherein the computer is programmed to present a display with the indication of at least one item derived from the second image data spatially correlated with items in the first field of view.

16. A contraband detection system adapted to detect contraband objects concealed in an item under inspection within an inspection area, the system comprising:
 a) a structure bordering the inspection area, the structure comprising:
  i) an exterior surface;
  ii) a heat generating member within the structure; and
  iii) a layer between the exterior surface and the heat generating member transparent to millimeter wave radiation; and
 b) a millimeter wave camera having a field of view, the millimeter wave camera being positioned such that a portion of the exterior surface adjacent the heat generating member is within the field of view.

17. The contraband detection system of claim 16 wherein the layer is a thermal insulator.

18. The contraband detection system of claim 16 wherein the layer comprises radome foam.

19. The contraband detection system of claim 16 wherein the layer comprises closed cell urethane foam.

20. The contraband detection system of claim 19 wherein the heat generating member comprises an electrical resistance heater.

21. The contraband detection system of claim 16 additionally comprising a layer absorptive of millimeter wave radiation.

22. The contraband detection system of claim 16 additionally comprising a plenum.

23. The contraband detection system of claim 16 additionally comprising a visible light camera.

24. A contraband detection system comprising:
 a) a first heated structure containing a first member emitting heat energy embedded therein;
 b) a millimeter wave camera facing the heated structure; and
 c) a second heated structure having a second member emitting heat energy embedded therein, the second heated structure being positioned such that the millimeter wave camera is disposed between the first heated structure and the second heated structure.

25. The contraband detection system of claim 24 additionally comprising a first temperature controller operatively coupled to the first heated structure to regulate the temperature thereof and a second temperature controller operatively coupled to the second heated structure to regulate the temperature thereof.

26. The contraband detection system of claim 25 wherein the first temperature controller and the second temperature controller each have a temperature setting and the temperature setting of the first temperature controller is lower than the temperature setting of the second temperature controller.

27. The contraband detection system of claim 24 wherein the first heated structure is heated internally to an internal temperature in excess of 90° F. and the second heated structure is internally heated to an internal temperature in excess of 120° F.

28. The contraband detection system of claim 27 wherein the second heated structure is internally heated to an internal temperature between 130° F. and 150° F.

29. The contraband detection system of claim 27 wherein the first heated structure comprises a wall of an enclosure and the second heated structure comprises an opposing wall of the enclosure.

30. An airport security checkpoint comprising:
 a) an enclosure having a millimeter wave camera imaging a field of view within the enclosure, the enclosure having a passage sized to allow a person to enter the field of view, the camera having a camera data output;

b) a baggage scanner having a scanner data output;

c) at least one computer having inputs coupled to the camera data output and the scanner data output, the at least one computer programmed to present, based on the camera data output and the scanner data output, an image for a passenger.

31. The airport security checkpoint of claim 30 wherein the passage has an opening and the security checkpoint additionally comprises a metal detector adjacent the opening.

32. The airport security checkpoint of claim 30 wherein the enclosure has a plurality of walls and the walls are temperature controlled.

33. The airport security checkpoint of claim 32 wherein the walls are temperature controlled by internal heating.

34. The airport security checkpoint of claim 30 additionally comprising a network providing a connection to a database storing data used in a program on the computer.

35. The airport security checkpoint of claim 34 wherein the network comprises a secure network and the database comprises an intelligence database.

36. The airport security checkpoint of claim 34 wherein the database comprises a database of updates for a program on the computer.

37. The airport security checkpoint of claim 30 additionally comprising at least one biometric sensor having a sensor output and the computer additionally has an input coupled to the sensor output and the computer is programmed to present, based on the camera data output, the scanner data output and the sensor output, an image for a passenger.

* * * * *